United States Patent
Wallen et al.

(10) Patent No.: US 6,455,493 B1
(45) Date of Patent: Sep. 24, 2002

(54) METHODS FOR USING HEAT SHOCK PROTEINS

(75) Inventors: Erik Wallen; Pope L. Moseley, both of Albuquerque, NM (US)

(73) Assignee: University of New Mexico, Albuquerque, NM (US)

( * ) Notice: Subject to any disclaimer, the term of this patent is extended or adjusted under 35 U.S.C. 154(b) by 0 days.

(21) Appl. No.: 09/276,468

(22) Filed: Mar. 25, 1999

Related U.S. Application Data

(63) Continuation-in-part of application No. 08/986,234, filed on Dec. 5, 1997, now Pat. No. 5,981,706, which is a continuation-in-part of application No. 08/934,139, filed on Sep. 19, 1997, now Pat. No. 6,066,716, which is a continuation-in-part of application No. 08/717,239, filed on Sep. 20, 1996, now Pat. No. 5,747,332.
(60) Provisional application No. 60/079,426, filed on Mar. 26, 1998.

(51) Int. Cl.$^7$ .............................................. A01N 37/18
(52) U.S. Cl. ......................... 514/2; 530/350; 530/827; 424/193.1; 424/184.1
(58) Field of Search ........................... 514/2; 530/827, 530/350; 424/193.1, 184.1

(56) References Cited

U.S. PATENT DOCUMENTS

| | | | |
|---|---|---|---|
| 5,114,852 A | 5/1992 | Yabusaki et al. | ............ 435/189 |
| 5,132,407 A | 7/1992 | Stuehr et al. | ............... 530/395 |
| 5,268,465 A | 12/1993 | Bredt et al. | .............. 435/252.3 |
| 5,320,941 A | 6/1994 | Young et al. | ............... 435/7.23 |
| 5,348,864 A | 9/1994 | Barbacid | .................... 435/69.1 |
| 5,348,945 A | 9/1994 | Berberian et al. | ............ 514/21 |
| 5,541,095 A | 7/1996 | Hirschberg et al. | ....... 435/172.3 |
| 5,550,214 A | 8/1996 | Eberlein et al. | ............ 530/328 |
| 5,614,192 A | 3/1997 | Vanderbark | ............... 424/185.1 |
| 5,830,464 A | 11/1998 | Srivastava | ............... 424/93.71 |
| 5,837,251 A | 11/1998 | Srivastava | ............... 424/193.1 |
| 5,935,576 A | 8/1999 | Srivastava | ............... 424/184.1 |
| 6,007,821 A | 12/1999 | Srivastava | ............... 424/193.1 |
| 6,165,737 A | * 12/2000 | Wang et al. | .................. 435/7.6 |

OTHER PUBLICATIONS

Baltz, "Vaccines in the treatment of Cancer," *Am. J. Health–Syst. Pharm.* (1995), 52:2574–2585.

Beckmann et al., "Interaction of Hsp70 with newly synthesized proteins: implications for protein folding and assembly," *Science* (1990), 248:850–4.

Blachere et al., "Heat Shock Protein Vaccines Against Cancer," *Journal Of Immunotherapy* (1993), 14:352–356.

Buchner, "Supervising the Fold: Functional Principals of Molecular Chaperones," *The FASEB Journal*, vol. 10, pp. 10–19, Jan. 1996.

Cai et al, "A Cloned Major *Schistosoma mansoni* Egg Antigen with Homologies to Small Heat Shock Proteins Elicits Th 1 Responsiveness," *Infection and Immunity* (May, 1996), vol. 64, No. 5, pp. 1750–1755.

Chopra et al., "TH1 pattern of cytokine secretion by splenic cells from pyelonephritic mice after in–vitro stimulation with hsp–65 of *Escherichia coli*," *J. Med. Microbiology* (Aug. 1997), vol. 84, No. 2, pp. 103–106.

Cohen, Irun R., "Short Anayltical Review: The Th1/Th2 Dichotomy, hsp60 Autoimmunity, and Type 1 Diabetes," *Clinical Immunology and Immunopathology* (1997), vol. 46, pp. 139–144.

Frankel, "Advances in Immunotoxin Biology and Therapy: A summary of the Fourth International Symposium on Immunitoxins." *Cancer Research* (1996), 56:926–932.

Gao et al., "Characterization of Nucleotide–Free Uncoating ATPase and Its Binding to ATP, ADP, and ATP Analogues," *Biochemistry* (1994), 33:2048–2054.

Gao et al., "Effect of Constitutive 70–kDa Heat Shock Protein Polymerization on Its Interaction with Protein Substrate" in *The Journal of Biological Chemistry*, vol. 271 (1996), 28: 16792–16797.

Gao et al., "Interaction of Nucleotide–Free HSC70 with Clathrin and Peptide and Effect of ATP Analogues," *Biochemistry* (1995) 34:11882–11888.

Gao et al., "Nucleotide Binding Properties of Bovine Brain Uncoating ATPase," *The Journal of Biological Chemistry* (1993), 269:8507–8513.

Georgopoulos et al., "Role of the Major Heat Shock Proteins as Molecular Chaperones," Annu. Rev. Cell Biol. 1993, pp. 602–634.

Gjertsen et al., "Vaccination with mutant ras peptides and induction of T–cell responsiveness in pancreatic carcinoma patients carrying the corresponding RAS mutation," *Lancet* (1995), 346:1399–1400.

Greene et al., Disassociation of Clathrin from Coated Vesicles by the Uncoating ATPase, *Journal of Biological Chemistry* (1990), 265:6682–6687.

Greene et al., "Effect of Nucleotide on the Binding of Peptides to 70–kDA Heat Shock Protein," *Journal of Biological Chemistry* (1995), 70:2967–2973.

Ha et al., ATPase Kinetics of Recombinant Bovine 70 kDA Heat Shock Cognate Protein and Its Amino–Terminal ATPase Domain, *Biochemistry*, (1994), 33:14625–14635.

Heike et al., "Heat shock protein–peptide complexes for use in vaccines," *Journal of Leukocyte Biology* (1996), 60:153–8.

(List continued on next page.)

*Primary Examiner*—Dwayne C. Jones
*Assistant Examiner*—C. Delacroix-Muirhei
(74) *Attorney, Agent, or Firm*—Jagtiani + Guttag

(57) ABSTRACT

The present invention provides a heat shock protein immunotoxin comprising: at least a fragment of a heat shock protein, the fragment being capable of being bound by an immune cell; and a toxin bound to the fragment. The present invention also provides a method for decreasing the number of immune cells in an individual using the heat shock protein immunotoxins of the present invention. In addition, the present invention provides a method for decreasing the number of immune cells in an organ using the heat shock protein immunotoxins of the present invention.

38 Claims, No Drawings

OTHER PUBLICATIONS

Kelleher et al., "Safety and immunogenicity of UB1 HIV–IMN octameric V3 peptide vaccine administered by subcutaneous injection," *AIDS Research & Human Retroviruses* (1997), 13:29–32.

Kolb et al., "Cytokine Gene–Expression in the BE Rat Pancreas: Natural Course and Impact of Bacterial Vaccines," *Diabetologia* (Dec. 1996), vol. 39, No. 12, pp. 1448–1454.

Kohno et al. "Regulation of Cytokine Production by Sugi Allergen–Pullulan Conjugate," Cellular Immunololgy (Oct. 1995), 168: 211–219.

Kuby, J., *Immunology*, (New York: W. H. Freeman, 1994) p. 432.

Lefkovits, *Immunological Methods Manual*, vol. 2, Chapter 9.11, (San Diego: Academic Press, 1997).

Lehninger, *Biochemistry*, (New York: Worth Publishers, 1970), p. 299.

Li et al., "A Critical Contemplation on the Roles of Heat Shock Proteins in Transfer of Antigenic Peptides During Antigen Presentation," *Behring Inst. Mitt.* (1994), 94:37–47.

Li et al., "Tumor rejection antigen gp96/grp94 is an ATPase: implications for protein folding and antigen presentation," *The EMBO Journal*, vol. 12, No. 8 (1993), 3143–3151.

Matzinger, "An Innate Sense of Danger," *Immunology* (1998), 10:399–415.

Matzinger et al., "Tolerance, danger, and the extended family," *Annual Review of Immunology*, (1994), vol. 12, pp. 991–1045.

Minami et al., "Regulation of the Heat–Shock Protein 70 Reaction Cycle by the Mammalian DnaJ Homolog, HSP40," *Journal of Biological Chemistry* (1999)271:19617–19624.

Mitra et al., "HLA–DR Polymorphism Modulates the Cytokine Profile of Mycobacterium leprae HSP–Reactive CD4+T Cells," *Clinical Immunology and Immunopathology* (Jan. 1997), vo. 82, pp. 60–67.

Moseley, "Mechanisms of heat adaptation: Thermotolerance and acclimization" in *J. Lab. Clin. Med.* (1994), 123:48–52.

Nandan et al., "A rapid single–step purification method for immunogenic members of the hsp family: validation and application," *Journal of Immunological Methods* (1994), 176:255–263.

Old, "Immunotherapy for cancer," *Scientific American* (1996), 275:142.

Palleros et al., "hsp70–Protein Complexes" in *The Journal of Biological Chemistry*, vol. 269 (1994), 18:13107–13114.

Palleros et al., "Interaction of hsp70 with unfolded proteins: Effects of temperatures and nucleotides on the kinetics of binding" in *Proc. Natl. Acad. Sci.* (Jul. 1991), 88:5719–5723.

Peng et al., "Purification of immunogenic heat shock protein70–peptide complexes by ADP–affinity chromatography," *Journal of Immunological Methods* (1997), 204: 13–21.

Polla et al., "Presence of hsp65 in bacterial extracts (OM–89): a possible mediator of orally–induced tolerance," *Experientia 51* (1995), Birkhauser Verlag, CH–4010 Basel/Switzerland, pp. 775–779.

Prasad et al., "Complex Formation between Clathrin and Uncoated ATPase," *Journal of Biological Chemistry*, (1994) 269:6931–6939.

Roman et al., "Delayed–type hypersensitivity elicited by synthetic peptides complexed with mycobacterial tuberculosis hsp70," *Immunology*, (1997), 90:52–56).

Roman et al., "Synthetic peptides non–covalently bound to bacterial hsp70 elicit peptide specific T–cell response in vivo," *Immunology*, (1996), 88:487–492.

Sadis et al., "Unfolded Proteins Stimulate Molecular Chaperone Hsc70 ATPase by Acclerating ADP/ATP Exchange," *Biochemistry*, (1992) 9406–9412.

Srivastava et al., "Heat shock protein–peptide complexes in cancer immunotherapy," *Current Opinion in Immunology* (1994), 6:728–732.

Srivastava, "Heat shock proteins in immune responses to cancer: the fourth paradigm," *Experientia* (1994), 50:1054–1060.

Srivastava et al., "Heat shock proteins transfer peptides during antigen processing and CTL priming," *Immunogenetics* (1994), 39:93–98.

Srivastava, "Peptide–Binding Heat Shock Proteins in the Endoplasmic Reticulum: Role in Immune Response to Cancer and in Antigen Presentation," *Advances in Cancer Research* (1993), 62:153–177.

Srivastava, "Purification of heat shock protein–peptide complexes for use in vaccination against cancers and intracellular pathogens," *Immunology Methods Manual* (1997)738–748.

Tamura et al, "Immunotherapy oftumors with autologous tumor–derived heat shock protein preparations," *Science* (1997), 278, 117–120.

Udono et al., "Comparison of Tumor–Specific Immunogenicities of Stress–Induced Proteins gp96, hsp90, and hsp 70," *Journal of Immunology* (1994), 5398–5403.

Udono et al., "Heat Shock Protein 70–associated Peptides Elicit Specific Cancer Immunity," *J. Exp. Med.* (1993), 178:1391–1396.

Welch et al., "Rapid Purificaiton of Mammalian 70,000–Dalton Stress Proteins: Affinity of the Proteins for Nucleotides," *Molecular and Cellular Biology* (Jun. 1985), 1229–1237.

* cited by examiner

METHODS FOR USING HEAT SHOCK PROTEINS

RELATED APPLICATIONS

The present application is based on U.S. Provisional Application No. 60/079,426, filed Mar. 26, 1998, the entire disclosure and contents of which is hereby incorporated by reference. The present application is also a continuation-in-part of U.S. patent application Ser. Nos. 08/717,239 filed Sep. 20, 1996 now U.S. Pat. No. 5,747,332, and 08/934,139, filed Sep. 19, 1997, now U.S. Pat. No. 6,066,716, and 08/986,234 filed Dec. 5, 1997, now U.S. Pat. No. 5,981,706, the entire disclosure and contents of which are hereby incorporated by reference.

BACKGROUND OF THE INVENTION

1. Field of the Invention

The present invention relates generally to treating diseases with immunotoxins.

2. Description of the Prior Art

In the field of treating diseases with immunotoxins, an ongoing problem has been to insure that the immunotoxins kill target cells and only target cells. As described in Frankel et al., "Meeting Report: Advances in Immunotoxin Biology and Therapy: A Summary of the Fourth International Symposium on Immunotoxins" in *Cancer Research* 56 (Feb. 15, 1996), pp. 926–932, in the case of immunotoxin treatments for cancer there are few treatments which can deliver an effective amount of a toxin to a cell and, and the toxicities which result from the treatments have generally been less than those for conventional chemotherapy.

SUMMARY OF THE INVENTION

In one aspect, the present invention provides a heat shock protein immunotoxin comprising: at least a fragment of a heat shock protein, the fragment being capable of being bound by an immune cell; and a toxin bound to the fragment.

In a second aspect, the present invention provides a method for reducing the number of at least one type of immune cells in an individual comprising the step of administering a heat shock protein immunotoxin to an individual in an amount sufficient to decrease the number of immune cells of at least one type in the individual, the heat shock protein immunotoxin comprising at least a fragment of a heat shock protein, the fragment being capable of being bound by an immune cell; and a toxin bound to the fragment.

In a third aspect, the present invention provides a method for reducing the number of at least one type of immune cells in an organ comprising the step of administering a heat shock protein immunotoxin to at least a portion of an organ in an amount sufficient to decrease the number of immune cells of at least one type in the organ, the heat shock protein immunotoxin comprising at least a fragment of a heat shock protein, the fragment being capable of being bound by an immune cell; and a toxin bound to the fragment.

DETAILED DESCRIPTION OF THE PREFERRED EMBODIMENT

Definitions

For the purposes of the present invention, the term "toxin" refers to any chemical or substance which kills cells, renders them inactive or causes them to be unable to perform their normal functions. Examples of such toxins include ricin, saporin, Shiga toxin, *Pseudomonas exotoxin*, radioactive isotopes (either alone or as part of a molecule), etc. Toxins suitable for use with the present invention may also include chemotherapeutic agents such as: bleomycin, methotrexate, cyclophosphamide, vinca alkaloids, adriamycin, cisplatin, etoposides, etc.

For the purposes of the present invention, the term "heat shock protein immunotoxin" refers to heat shock protein-peptide complexes where the peptide is a toxin, immunotoxins in which a heat shock protein or a fragment of a heat shock protein is covalently bound to a toxin, and immunotoxins in which a heat shock protein or a fragment of a heat shock protein is combined with a toxin comprising a protein oligonucleotide sequence or molecule.

For the purposes of the present invention, the terms "bind" and "binding" refer to both covalent and non-covalent binding.

For the purpose of the present invention, the term "fragment" can refer to a portion of a heat shock protein or an entire heat shock protein.

For the purposes of the present invention, the term "oligonucleotide" refers to any oligonucleotide, including double and single-stranded DNA, RNA, PNAs (peptide nucleic acids) and any sequence of nucleic acids, either natural or synthetic, derivatized or underivatized.

For the purposes of the present invention the term "peptide" refers to all types of peptides and conjugated peptides including: peptides, proteins, polypeptides, protein sequences, amino acid sequences, denatured proteins, antigens, oncogenes and portions of oncogenes.

For the purposes of the present invention the term "individual" refers to either an individual person or animal from whom a cell lysate, heat shock protein, or peptide is obtained or an individual patient who is treated according to a method of the present invention.

For the purposes of the present invention, the term "immune cells" refers to B lymphocytes, T lymphocytes, antigen presenting cells, macrophages, monocytes, natural killer cells, and dendritic cells.

For the purposes of the present invention, the term "antigen presenting cells" refers to B lymphocytes, macrophages, and dendritic cells.

For the purposes of the present invention, the term "organ" is used in the broad sense of this term to include such organs as the skin, bone marrow, etc.

Description

The present invention provides a method for specifically destroying or inhibiting cellular function of immune cells which bind heat shock proteins or portions of heat shock proteins.

Heat shock proteins (HSPs) which are non-covalently bound to peptides as HSP-peptide complexes have been shown to be capable of inducing T-cell mediated responses to tumor antigens, see for example Udono et al. "Heat shock protein 70-associated peptides elicit specific cancer immunity" in *Journal of Experimental Medicine* (1993) 178: 1391–1396; and Tamura et al. "Immunotherapy of tumors with autologous tumor-derived heat shock protein preparations" in *Science* (1997), 278:117–120. HSP-peptide complexes have also been shown to be capable of inducing T-cell mediated responses to viral antigens as described in Roman et al., "Synthetic peptides non-covalently bound to bacterial HSP 70 elicit peptide specific T-cell responses in vivo in *Immunology* (1996), 88:487–492. HSPs covalently bound to antigens as fusion proteins have also be shown to elicit a T-cell specific response, see for example, Suzue, "Heat shock proteins as vehicles for antigen delivery into the major histocompatibility complex I presentation pathway" in *Proceedings of the National Academy of Sciences* (1997), 94:13146–13151. HSPs have also been shown to be important in the recognition structure for NK cells, see for example Multhoff et al., "Heat shock protein 72 on tumor cells: a recognition structure for NK cells" in *The Journal of Immunology* (1997), 158:4341–4350 and gamma delta T-cells, see for example Wei et al., "Induction of autologous tumor killing by heat treatment of fresh human tumor cells: involvement of γδ T cells and heat shock protein 70, in Cancer Research (1996), 56:1104–1110.

Toxins linked to antibodies have been used to specifically target cancer cells as described by Siegall et al., "Immunotoxins as cancer chemotherapeutic-agents" in *Drug Development Research*, v. 34(#2), (Feb. 1995), pp. 210–219. Toxins have also been linked as a fusion protein to human granulocyte-macrophage colony-stimulating factor by Burbage et al., "Ricin fusion toxin targeted to human granulocyte-macrophage colony-stimulating factor-receptor is selectively toxi to acute myeloid-leukemia cells" in *Leukemia Research*, v. 21 (#7), (Jul. 1997). pp. 681–690; and Frankel et al. "112 fused to lectin-deficient ricin is toxic to human leukemia -cells expressing the 112 receptor" in *Leukemia*, v. 11(#1), (Jan. 1997), pp. 22–30.

However, no one has investigated the possibility of using heat shock proteins as cell-specific carriers of toxins and agents capable of inhibiting the cellular function of immune cells. Since HSPs appear to be recognized by a variety of immune cells, toxin or cellular pathyway inhibitors linked to heat shock proteins may be a very useful tool.

The present invention relies on the fact that heat shock proteins are recognized by numerous cells in the immune system. The cells that are known to respond in the presence of heat shock proteins include T-cells, macrophages, dendritic cells, and B-cells. The toxin linked heat shock proteins of the present invention may provide a means to deplete these cells in circumstances where it is desirable to do so. Although it is not clearly understood at the present time which cells react to specific heat shock proteins, it is conceivable that individual heat shock proteins could be used to knock out specific sub-groups of immune cells.

Suitable heat shock proteins for the present invention include the heat shock proteins listed n U.S. Pat. No. 5,747,332. These HSPs include: members of the hsp60family, hsp70 family, hsp90 family and the hsp104-105 family. Members of the hsp60 family include hsp60, hsp65, rubisco binding protein, and TCP-1 in eukaryotes; and GroE1/GroES in prokaryotes; Mif4, and TCP1alpha and beta in yeast. Members of the hsp70 family include DnaK proteins from prokaryotes, Ssa, Ssb, and Ssc from yeast, hsp70, Grp75 and Grp78(Bip) from eukaryotes. Members of the hsp90 family include hsp90, gp96 and grp94. Members of the hsp104-105 family include hsp105 and hsp110.

Potential toxins which may be used in the complexes of the present invention include ricin, saporin, bryodin, Diptheria toxin and *Pseudomonas exotoxin*. Immunotoxins which may be used in the present invention's cancer therapeutic-agents have been described in Siegall et al., Drug Development Research, v. 34(#2), pp. 210–219 (Feb. 1995), the entire disclosure and contents of which is hereby incorporated by reference. The heat shock proteins of the present invention may also be used to deliver toxins such as specific inhibitors of cellular processes such as inhibitors of signal transduction, ion channel function, etc.

Another use of the heat shock protein immunotoxins of the present invention is to deliver chemotherapeutic agents to target cells to treat conditions such as cancer, autoimmune diseases, asthma, etc. One of the advantages using the heat shock protein immunotoxins of the present invention over prior chemotherapy treatments is that using the immunotoxins of the present invention allow for chemotherapeutic agents to be delivered to specific target cells. Because the immunotoxins of the present invention allow for the delivery of the chemotheropeutic agents to specific target cells, the amount of chemotherapeutic agent used in the methods of the present invention may be greatly decreased when compared to conventional chemotherapy treaments, thus avoiding the numerous systemic side effects associated with conventional chemotherapy treatments.

In the complexes of the present invention, the toxins may be non-covalently linked to the heat shock proteins either as peptides (in the peptide binding grooves of individual HSPs), covalently linked to the HSPs, or by the construction of a fusion protein.

Some of the methods which can be used to non-covalently link toxins which are peptides to heat shock proteins as part of an ADP-HSP-peptide complex are described in U.S. Pat. No. 5,747,332, the entire disclosure and contents of which is hereby incorporated by reference. By adding an appropriate peptide toxin to an ADP-column containing a particular heat shock protein bound to the ADP in the column, the peptide toxin will bind to the ADP-heat shock protein complex. The resulting ADP-heat shock protein-peptide toxin complex may then be eluted by running a solution containing ADP through the column.

Methods which can used to covalently link toxins to HSP include methods such as those described in U.S. Pat. Nos. 4,714,759 and 5,645,836, the entire disclosure and contents of which are hereby incorporated by reference.

In making a fusion protein, heat shock protein DNA sequences or fragments of heat shock protein DNA sequences may be combined with toxic protein DNA sequences or molecules using techniques known in the art. Fusion proteins containing sequences of both heat shock proteins or heat shock protein fragments and toxins can then easily be created. Methods which can be used to link toxins to HSP as part of a fusion protein include methods such as those described in U.S. Pat. No. 5,696,237, the entire disclosure and contents of which is hereby incorporated by reference.

The toxin-linked heat shock proteins complexes of the present invention are particularly useful for treating autoimmune diseases, diseases where the immune system attacks self proteins. The complexes of the present invention may also be used to temporarily debilitate an individual's immune system before and after transplanting an organ. In addition, the complexes of the present invention may be used to inhibit specific intracellular pathways of immune cells. In general, the present invention is useful to treat diseases where it is desirable to reduce the effectiveness of an individual's immune system.

The heat shock protein immunotoxins of the present invention may be used to kill antigen presenting cells (APCs) and other immune cells having receptors which bind at least a portion of a heat shock protein. The immunotoxins of the present invention may also be useful in treating diseases such as psoriasis. Lupus, or other diseases and autoimmune diseases in which APCs, or other immune cells with receptors which bind at least a portion of a heat shock protein, mediate an inappropriate immune response.

The heat shock protein immunotoxins of the present invention are particularly useful for treating auto-immune diseases, diseases where the immune system attacks self proteins because the immune system mistakes self-proteins for bacterial proteins. The immunotoxins of the present invention may also be used to temporarily debilitate an individual's immune system before and after transplanting an organ. The heat shock protein immunotoxins of the present invention may also be useful in depleting APCs in transplanted organs to increase the chance that the organ will not be rejected, see *Seminars in Immunology* (1998), 10:399. In addition, the complexes of the present invention may be used to inhibit specific intracellular pathways of immune cells. In general, the present invention is useful to treat diseases where it is desirable to reduce the effectiveness of an individual's immune system.

The immunotoxins of the present invention can be administered in any conventional way for treating individual with a drug such as by injecting a solution containing a immunotoxin of the present invention into an individual's bloodstream, topically applying a solution containing a immunotoxin of the present invention on a particular part of a tissue or organ. For example, a solution containing the immunotoxin may be applied to the skin of a patient suffering from psoriasis. When the immunotoxins of the present invention are used to treat organs which are to be transplanted into an individual, a immunotoxin of the present invention may be topically applied to the organ, the organ may be immersed in a solution of the immunotoxin, or the organ may be treated with perfusion techniques prior to the transplantation procedure. In perfusion, an organ is treated with a solution by using the blood vessels associated with the organ to administer the solution throughout the organ.

The present invention will now be described by way of example.

EXAMPLE 1

Prior to liver transplantation, the organ is perfused with hsp70-ricin immunotoxin complex for 30 minutes on ice. Immediately prior to transplantation, the organ is perfused with saline or other appropriate buffer.

EXAMPLE 2

In a bone marrow transplant, donor marrow is incubated with gp96-saporin immunotoxin on ice, rinsed, and then infused into the marrow of a recipient. This procedure reduces the complications of graft versus host disease.

EXAMPLE 3

During transplantation surgery, the wounds of a patient are bathed in hsp70-ricin immunotoxin solutions, causing the death of immune cells activated by surgical damage.

EXAMPLE 4

In psoriasis patients, activated macrophages are killed by topical application of an hsp70-saporin immunotoxin containing ointment.

Although the present invention has been fully described in conjunction with the preferred embodiment thereof, it is to be understood that various changes and modifications may be apparent to those skilled in the art. Such changes and modifications are to be understood as included within the scope of the present invention as defined by the appended claims, unless they depart therefrom.

What is claimed is:

1. A heat shock protein immunotoxin comprising:

a heat shock protein;

a toxin bound to said heat shock protein, said toxin comprising a peptide; and

ADP complexed with said heat shock protein.

2. The immunotoxin of claim 1, wherein said toxin is covalently bound to said fragment.

3. The immunotoxin of claim 1, wherein said toxin is non-covalently bound to said fragment.

4. A heat shock protein immunotoxin comprising:

at least a fragment of a heat shock protein, said fragment being capable of being bound by an immune cell; and a toxin bound to said fragment, wherein said immunotoxin comprises a fusion protein.

5. A heat shock protein immunotoxin comprising:

at least a fragment of a heat shock protein, said fragment being capable of being bound by an immune cell; and a toxin bound to said fragment, wherein said toxin comprises ricin.

6. A heat shock protein immunotoxin comprising:

at least a fragment of a heat shock protein, said fragment being capable of being bound by an immune cell; and a toxin bound to said fragment, wherein said toxin comprises saporin.

7. A heat shock protein immunotoxin comprising:

at least a fragment of a heat shock protein, said fragment being capable of being bound by an immune cell; and a toxin bound to said fragment, wherein said toxin comprises a radioactive isotope.

8. A heat shock protein immunotoxin comprising:

at least a fragment of a heat shock protein, said fragment being capable of being bound by an immune cell; and a toxin bound to said fragment, wherein said toxin comprises a chemotherapeutic agent.

9. A method for reducing the number of at least one type of immune cells in an individual comprising the step of administering a heat shock protein immunotoxin to an individual in an amount sufficient to decrease the number of immune cells of at least one type in said individual, said heat shock protein immunotoxin comprising at least a fragment of a heat shock protein, said fragment being capable of being bound by an immune cell; and a toxin bound to said fragment.

10. The method of claim 9, wherein said immunotoxin comprises a toxin bound to a heat shock protein.

11. The method of claim 10, wherein said toxin comprises a peptide, and said peptide is complexed with said heat shock protein.

12. A method for reducing the number of at least one type of immune cells in an individual, comprising the step of administering a heat shock protein immunotoxin to an individual in an amount sufficient to decrease the number of immune cells of at least one type in said individual, said heat shock protein immunotoxin comprising: a heat shock protein; a toxin bound to said heat shock protein, said toxin comprising a peptide; and ADP complexed with said heat shock protein.

13. The method of claim 9, wherein said toxin is covalently bound to said fragment.

14. The method of claim 9, wherein said toxin is non-covalently bound to said fragment.

15. The method of claim 9, wherein said immunotoxin comprises a fusion protein.

16. The method of claim 9, wherein said toxin comprises ricin.

17. The method of claim 9, wherein said toxin comprises saporin.

18. The method of claim 9, wherein said toxin comprises a radioactive isotope.

19. The method of claim 9, wherein said at least one type of immune cells consists of one type of immune cells.

20. The method of claim 9, wherein said at least one type of immune cells comprises at least one type of antigen presenting cells.

21. The method of claim 9, wherein said immunotoxin is administered by injecting said immunotoxin into said individual.

22. The method of claim 9, wherein said immunotoxin is administered by topically applying said immunotoxin to the skin of said individual.

23. The method of claim 9, wherein said toxin comprises a chemotherapeutic agent.

24. A method for reducing the number of at least one type of immune cells in an organ comprising the step of administering a heat shock protein immunotoxin to at least a portion of an organ in an amount sufficient to decrease the number of immune cells of at least one type in said organ, said heat shock protein immunotoxin comprising at least a fragment of a heat shock protein, said fragment being capable of being bound by an immune cell; and a toxin bound to said fragment.

25. The method of claim 24, wherein said immunotoxin comprises a toxin bound to a heat shock protein.

26. The method of claim 24, wherein said toxin comprises a peptide, and said peptide is complexed with said heat shock protein.

27. A method for reducing the number of at least one type of immune cells in an organ comprising the step of administering a heat shock protein immunotoxin to at least a portion of an organ in an amount sufficient to decrease the number of immune cells of at least one type in said organ, said heat shock protein immunotoxin comprising: a heat shock protein; a toxin bound to said heat shock protein, said toxin comprising a peptide; and ADP complexed with said heat shock protein.

28. The method of claim 24, wherein said toxin is covalently bound to said fragment.

29. The method of claim 24, wherein said toxin is non-covalently bound to said fragment.

30. The method of claim 24, wherein said immunotoxin comprises a fusion protein.

31. The method of claim 24, wherein said toxin comprises ricin.

32. The method of claim 24, wherein said toxin comprises saporin.

33. The method of claim 24, wherein said toxin comprises a radioactive isotope.

34. The method of claim 24, wherein said at least one type of immune cells consists of one type of immune cells.

35. The method of claim 24, wherein said at least one type of immune cells comprises at least one type of antigen presenting cells.

36. The method of claim 24, wherein said immunotoxin is administered to said portion of said organ by perfusion.

37. The method of claim 24, wherein said immunotoxin is administered to substantially all of said organ.

38. The method of claim 24, wherein said toxin comprises a chemotherapeutic agent.

* * * * *